United States Patent [19]

Cichanski

[11] Patent Number: 4,866,986
[45] Date of Patent: Sep. 19, 1989

[54] METHOD AND SYSTEM FOR DUAL PHASE SCANNING ACOUSTIC MICROSCOPY

[75] Inventor: Frank J. Cichanski, Elgin, Ill.

[73] Assignee: Sonoscan, Inc., Bensenville, Ill.

[21] Appl. No.: 245,003

[22] Filed: Sep. 15, 1988

[51] Int. Cl.$^4$ ............................................. G01N 29/04
[52] U.S. Cl. ......................................... 73/600; 73/606
[58] Field of Search ................. 73/588, 598, 599, 600, 73/620, 629; 358/112; 367/110

[56] References Cited

U.S. PATENT DOCUMENTS 4,620,444  11/1986  Young ................................... 73/606

OTHER PUBLICATIONS

Adams, T. "Using the Precision C-Sam for Bilateral Inspection of Die Attach" Microelectronic Manufacturing and Testing Jun., 1987.

Lynnworth, L. C. "Attenuation Measurements Using the Pulse-Echo AB Method, Without Multiple Echo Reverberations in Specimen" Jan., 1973.

*Primary Examiner*—Stewart J. Levy
*Assistant Examiner*—Lawrence G. Fess
*Attorney, Agent, or Firm*—Kinzer, Plyer, Dorn, McEachran & Jambor

[57] ABSTRACT

In a scanning acoustic microscope of the reflection type, in which an object is insonified with a series of ultrasonic acoustic pulses in accordance with a preselected scanning pattern and reflected acoustic echo pulses are received and employed to generate an initial electrical signal comprising a sequence of electrical pulses having amplitudes and polarities representative of the magnitudes and phases of the echoes, a directly readable unified interpretative display image is produced from the entire electrical signal; that image includes the usual scanning position and depth information determined by timing of the electrical pulses, together with complete transition information regarding the nature of acoustic impedance changes, based on both the amplitudes and the polarities of those pulses. A compared dual integration method and system, with related gating and display enhancement techniques, comprises the preferred embodiment.

28 Claims, 2 Drawing Sheets

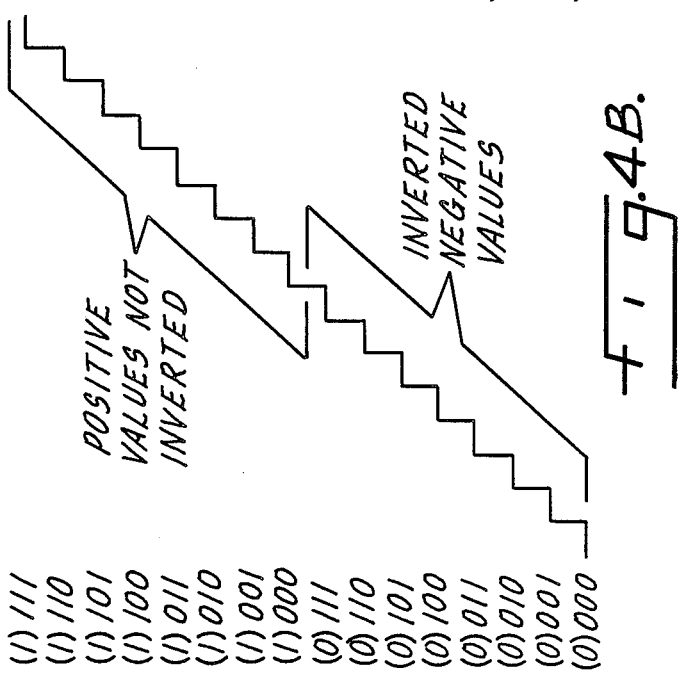
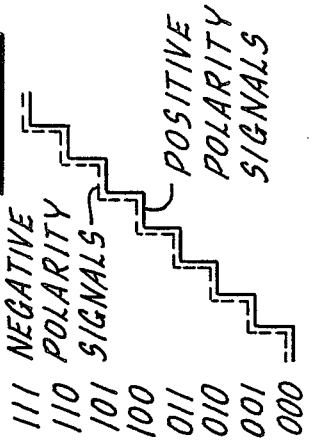
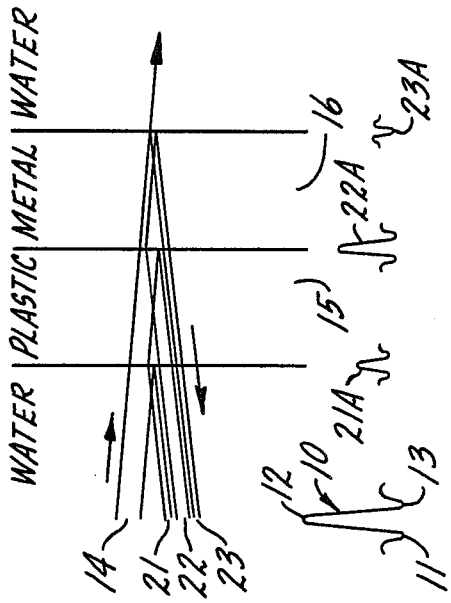
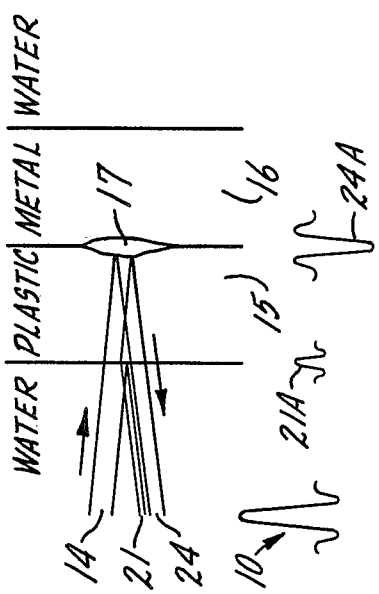
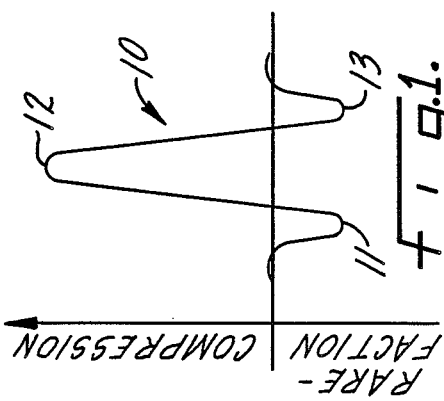
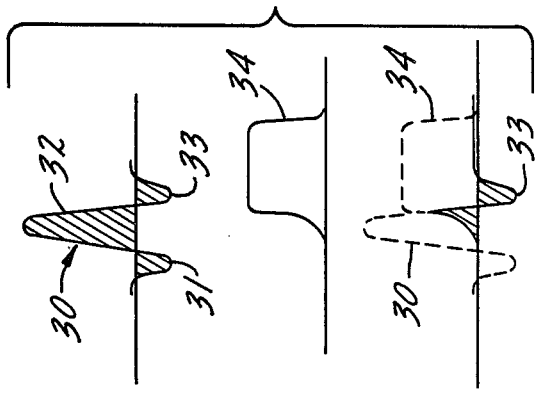

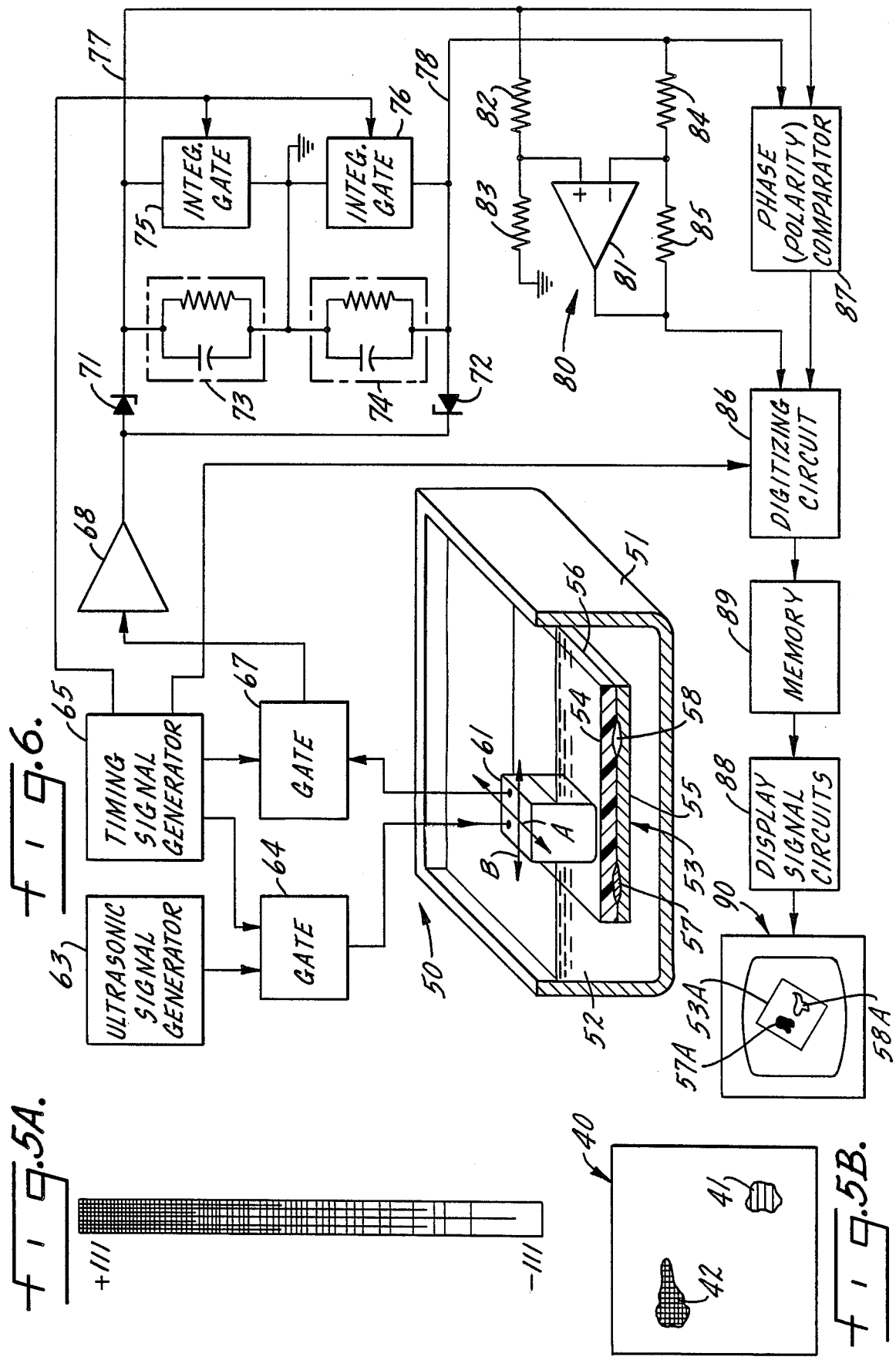

METHOD AND SYSTEM FOR DUAL PHASE SCANNING ACOUSTIC MICROSCOPY

BACKGROUND OF THE INVENTION

The scanning acoustic microscope (SAM) has become a convenient and familiar tool for inspection and quality control in manufacturing and other industrial applications. One of the more effective devices of this kind employs a C-mode scanning mechanism, with the object under investigation insonified by a series of ultrasonic acoustic pulses; ultrasound reflections from the object are received and are utilized to generate an initial electrical signal. That electrical signal, in turn, is used to develop an image of the object, an image that can focus on varying transition levels within the object. A basic system of this kind is described in the article "Using the Precision C-SAM for Bilateral Inspection of Die Attach" in *Microelectronic Manufacturing and Testing*, June, 1987.

One diffuclty in operation of a reflection-mode SAM has been distinguishing "hard" discontinuities from "soft" imperfections. A "hard" discontinuity is a solid that is more rigid than adjacent material in the object, whereas a "soft" imperfection may be a spongy discontinuity or even a gas pocket or void. In most SAMs it is difficult to distinguish between the two because the magnitudes of the ultrasonic echoes from them may be similar or even essentially equal, though the phases of the echoes are distinguishable. Some SAMs have included means to switch from an image of one phase (polarity) to an image of the other phase. This is not really satisfactory, however, because the investigator using the SAM cannot see a unified image of all of the available information.

SUMMARY OF THE INVENTION

It is an object of the invention, therefore, to provide a new and improved method and system for utilization of all of the information present in the ultrasonic echoes in a reflection-type scanning acoustic microscope, from at least one level in an object, to generate a unified display that effectively simultaneouly shows and distinguishes between "hard" and "soft" discontinuities in the object.

Another object of the invention is to provide a new and improved display method and system for a reflection mode SAM that preserves and uses all phase information from the ultrasonic echoes, concurrently with amplitude information, in a unified image, and that is simple and economical in construction and reliable in operation.

Accordingly, in one aspect the invention relates to the method of examining internal structure in an object by reflection mode scanning acoustic microscopy, comprising the steps of:

A. generating a series of acoustic pulses of ultrasonic frequency and predetermined magnitude;

B. insonifying an object with the acoustic pulses from step A, with predetermined timing and in accordance with a preselected scanning pattern;

C. receiving ultrasonic pulse echoes reflected from the object and developing an initial electrical signal comprising a sequence of electrical pulses of varying amplitudes and polarities representative of the magnitudes and phases, respectively, of the ultrasonic pulse echoes; and X. producing a unified image representative of structure of the object, the unified image simultaneously displaying positions, magnitudes, and directions of acoustic impedance transitions for at least one depth level of the object, in which image:

1. positions of the acoustic transitions in the image and the image level in the object are determined by the timing of the pulses in the initial electrical signal,
2. transitions between differing acoustic impedances at the surfaces of and within the object are determined by the amplitudes of the pulses in the initial electrical signal, and
3. increases and decreases in acoustic impedance, in transitions at the surfaces of and within the object, are determined by the polarities of the pulses in the initial electrical signal.

In another aspect the invention relates to a display system for a scanning acoustic microscope of the kind comprising transducer means for generating a series of acoustic pulses of ultrasonic frequency and predetermined magnitude, acoustic scanning means for directing the acoustic pulses to impinge upon and insonify an object with predetermined timing and in accordance with a preselected scanning pattern, and receiver means for receiving ultrasonic pulse echoes reflected from the object and developing an initial electrical signal of varying amplitude and polarity representative of the magnitude and phase, respectively, of the ultrasonic pulse echoes. The display system comprises amplifier means, connected to the receiver means, for generating an amplitude content signal representative of amplitude of the initial electrical signal, independent of polarity, comparator means, connected to the receiver means, for generating a polarity content signal representative of polarity of the initial electrical signal, independent of amplitude, and display means, actuated by the content signals, for displaying a unified image of the object in which acoustic impedance transitions for at least one depth level of the object from which echoes of different phases occur are clearly distinguished from each other in the image despite similarities, however close, in the magnitudes of those echoes.

BRIEF DESCRIPTION OF THE DRAWINGS

FIG. 1 illustrates a preferred waveform for an ultrasonic pulse employed in a reflection mode scanning acoustic microscope (SAM):

FIGS. 2A and 2B illustrate the nature of echoes in a reflection mode SAM employing the pulse waveform of FIG. 1;

FIG. 3 illustrates the effect of inaccurate gating on the operation of a reflection mode SAM;

FIGS. 4A and 4B illustrate a technique for increasing the overall range of image gradations, based on phase information, in operation of a reflection mode SAM;

FIGS. 5A and 5B show elements of imaging in one embodiment of the invention; and FIG. 6 is a partly schematic block diagram of an image display system according to one embodiment of the invention.

DESCRIPTION OF THE PREFERRED EMBODIMENTS

In a reflection mode scanning acoustical microscope (SAM) a series of ultrasonic pulses, as sent to the target object, are made to take on a given waveform by appropriate means including a pulse generator, matching networks, and other associated circuitry. Although many different pulse formats are used, including bursts of single, multiple, or modulated frequencies, and bursts of various durations, the acoustic pulse form 10 most often elected, for a variety of reasons, is one which begins with a dip 11, then a sharp rise 12, and finally another dip 13, as shown in FIG. 1. Pulse 10 can be made to have the minimum amount of extraneous frequency components for a discontinuous pulse of the very brief duration required for good temporal resolution. In most media, the reduction of sidebands is a positive attribute, because it minimizes the amount of group delay distortion (dispersion in time of different frequency components), and thus leads to the sharpest returned echo. When a source of a single pure frequency is turned on and off rapidly, however, the resulting output signal, whether electrical or acoustical, is no longer that same pure frequency. Over the interval of the on-going and off-going, a range of frequency components are generated. On the one hand, it is desired to turn the signal on and off as rapidly as possible so that the pulse is a sharp single event in time. On the other hand, it is desired that no new frequencies be introduced, also for the purpose of making the pulse sharp and discrete. The two sides of this coin are incompatible, ultimately, and the best compromise between them is a pulse of roughly the form 10 as shown in FIG. 1.

When an acoustical pulse encounters any discontinuity (any change of the acoustic impedance of the medium through which it is traveling), part of its energy is reflected. It is these echoes that a reflection mode acoustic microscope receives and eventually employs to display an image of internal features of the target object. Various types of information are present in the returned pulse. The time delay between radiation and reception gives an accurate index of the depth, or distance in the direction of travel, of the discontinuity. The position from which the pulse is recovered, also a function of time, enables mapping of the discontinuity in the two dimensions perpendicular to the direction of insonification. The magnitude of the pulse echo is related to both the size of the discontinuity (if it is nearly equal to, or smaller than the sonic pulse at the position of reflection), and to the disparity between the acoustic impedances across the the discontinuity. This is the information usually used in SAM systems.

Another type of information is also present in the reflected sonic pulses. It is somewhat more subtle, but can be of immense importance in interpretation of the echoes. This is the phase of the signal. FIG. 1 shows the central peak 12 of pulse 10 as a compression, pointed in an upward direction. In fact, this orientation is quite arbitrary, though conventional. Not only could the acoustic pulse 10 be represented with an inverted sequence of compression/rarefaction, but an oscilloscope could also be arranged to show an electrical signal corresponding to pulse 10 in an inverted posture with equal accuracy. Nevertheless, within the constraints of a fixed and consistent reference frame, the echoes which return from a sonic pulse are most often merely smaller-amplitude copies of the original pulse (such less energy returns in each echo). Furthermore, these reduced reflection copies can be either "up-side-down" or "up-side-up".

Whether an echo returns "up" or "down" is not arbitrary. When the pulse of ultrasound encounters a region of higher acoustic impedance than it previously traveled, the echo is "up". On the other hand, if the impedance is reduced rather than increased, the echo is "down". In the extreme case of an open discontinuity such as a gas space or a vacuum, the echo is "down", and essentially all energy is returned; that is virtually no energy is transmitted beyond the discontinuity and a very strong inverted echo is returned.

Consider the two SAM situations illustrated in FIGS. 2A and 2B; in each, a series of ultrasonic pulses 14, of assumed waveform 10, is used to examine the internal structure of a plastic-metal laminate. In FIG. 2A the plastic 15 is assumed to be consistently well bonded to a metal member 16. In FIG. 2B, however, there is a void 17 between the plastic and the metal.

In FIG. 2A a first series of echoes or reflections 21 occurs because plastic has a higher acoustic impedance than water. Each echo is returned upright; see pulse form 21A. The change in impedance from water to plastic is limited, as regards the acoustic impedance increase, so that only a limited fraction of the ultrasonic energy comes back in echo 21. A reflection 22 of greater magnitude occurs when the discontinuity at the plastic-metal interface is encountered by beam 14. The bond here is good. The much higher acoustic impedance of the metal returns a large part of the energy, again in an upright mode; see pulse echo 22A. A different reflection 23 results when the remaining energy of the pulse sequence 14, having passed through metal 16, meets the water at the exit side. Here too there is an impedance mismatch, but this time there is a phase reversal, because the impedance of water is much less than of the metal. See pulse waveform 23A.

In FIG. 2B the echo or reflection 21 returns because plastic has a higher acoustic impedance than water. The echo is returned upright as shown by pulse 21A, the same as in FIG. 2A. But a different reflection 24 occurs when the back face of plastic 15 is reached by pulses 14. Metal 16, though in place, is not bonded to plastic 15. Instead there is an open discontinuity 17. Gap 17, whether vacuum or air-space, will not transmit ultrasound and therefore echos all the incident energy in a reflection 24. Stated differently, the acoustic impedance of void 17 is zero. Moreover, the energy echo, pulse waveform 24A, is inverted.

In each case, FIGS. 2A and 2B, the sonic energy incident upon the rear surface of plastic 15 is the same; call it $A_I$. The amplitude of each reflected pulse (e.g., 21A, 22A, 23A, 24A) is determinable by the formula $$A_R = A_I(Z_2 - Z_1)/(Z_2 + Z_1),$$

where $A_R$ is the echoed energy, $Z_1$ is the acoustic impedance of the first material (plastic 15), and $Z_2$ is the impedance of the second material (metal 15 or void 17). Choosing a typical value, we have $Z_1 = 3 \times 10^6$. In FIG. 2A, $A_R = 17/23 = 0.74$ (value near unity) but in FIG. 2B $A_R = -3/3 = -1$. These values have approximately the same magnitude. The minus sign for FIG. 2B indicates a signal inversion.

Determination of the difference between the two cases illustrated in FIGS. 2A and 2B can be of critical importance in investigating certain objects. An example is the discrimination between the inclusion of a "hard" speck, and an equal-sized "soft" speck, or void, within a sample. Without the ability to discriminate phase reversals, it may be difficult or impossible to determine which type of feature is present.

The effects of variations in the acoustic impedance of an inclusion reflecting the insonifying pulses, as applied to both magnitude and phase, are quite interesting. When the impedance is equal to that of the surrounding medium, no echo is returned of either polarity. Positing two differing inclusions, one twice the acoustic impedance of the preceding medium, and the other half that acoustic impedance, the echoes returned from such inclusions have essentially the same magnitudes. This is basically the mathematical operation of taking their "absolute value", i.e. disregarding their sign. Using the phase of the echo as the sign, however, the signed-amplitudes can be mapped into twice the cartesian space, developing a much more meaningful picture of the internal structure of the object examined. The echoes fill a natural continuum, proceeding from extreme inverted signals at one end of the range, through signals of small amplitude, to zero amplitude at the center of the range, then through increasing amplitudes to large non-inverted amplitudes at the other extreme of the range. Brightness, color, or a combination of the two can be used to incorporate all of the available information simultaneously in a unified display showing one or more levels within the scanned object, an image that is much more informative and more readily interpreted than a conventional SAM display. Thus, a conventional amplitude-only SAM image, one phase at a time, is somewhat analogous to a polygraph that can only determine a degree of emotional stress, but cannot distinguish pain from pleasure. The task therefore is twofold: detection of the phase and the meaningful display/interpretation of all phase data simultaneously in operation of a reflection mode SAM.

The amplitude and polarity of an electrical signal can each be determined in a number of well-known ways. However, peculiarities in ultrasonic microscopy make some of these techniques rather useless. Thus, a returned echo may actually be not one, but several echos, each coming from a slightly different place within the cone of insonification, displaced either laterally or axially from each other. Lateral displacement generally comes from an extended sheet of discontinuity not strictly at the focal point; in this case all the echo portions arrive at the same time.

It is the axial displacement of several echos which must be discriminated. This is done by electronic gating, using devices of many forms. Because mechanical gating ahead of the acoustic receiver of the Sam is impractical, any and all reflection signals are allowed to impinge upon the acoustic sensor that developes the initial electrical signal in the SAM. Preliminary gating can be accomplished merely by enabling operation of the receiver only for time periods corresponding to a sequence of intended gating intervals. In another gating technique, the receiver transducer can be allowed to operate continually, producing electrical signals representative of any and all ultrasonic energy echoes, with gating accomplished effectively by reading only the signals that occur at the opening and closing moments of a virtual gate. Gating may also be effected by integrating or otherwise processing the electrical signal only during predetermined gating intervals, and using the results to determine the signal present. If any of these methods, or variations, are adequately engineered, the results can be useful. These gating techniques, and others, can also be employed in various combinations for enhanced and more informative displays.

The placement in time of a gating "window" can be done by several methods, and in many conceivable systems. Three popular modes are:

(1) By strict delay from the time of acoustic pulse launching;

(2) By strict delay from the time of the first returned echo (at the outer surface of the target), providing an "internal standard" of the depth of subsequent echoes; and (3) By taking a series of different gating intervals, originally timed from one or the other of the first two means, and thus developing a multiple level view, within the constraints of beamwaist resolution, etc. The present invention can incorporate any or all of these gate window possibilities, especially when multiple memory plane options are included.

A complication arising in the detection of the phase of an acoustic pulse echo, usually represented by the polarity of an electrical signal, is that if a gating interval 34 truncates the first two excursions 31 and 32 of a reflection signal 30, as in FIG. 3 (or for that matter, the last two excursions, 32 and 33), then the reading of the largest excursion within the gating interval 34 will not be the larger central peak 32 (or valley, as the case may be). Instead, the misplaced window 34 will cause the pulse to be interpreted as constituting, as its significant component, the smaller terminal valley 33 (or, in the other case, the corresponding terminal or initial small peak). But the terminal and initial excursions (31 and 33) each have a phase (polarity) opposite from that of the large central excursion 32. Thus, the reading of the phase or polarity can be in error if the gating method is not adequately synchronous, but instead cuts off half or more of the relevant pulse form.

There are a number of methods for determining the phase of a reflected ultrasonic signal, as represented by the polarity of an electrical signal. One simple method is a "flip-flop-flip" technique. This method, which can be extremely fast, does not rely on precision measurement of amplitudes of the various excursions or on comparison of them. It presumes that:

(1) The pulse form of the echo contains only three excursions of sufficient magnitude to be detected, and that these are either dip-PEAK-dip or peak-DIP-peak.

(2) there are no other echoes close enough in time so that either the initial or terminal excursion of the pulse is cancelled to below detectable magnitude.

(3) The gating expressly and accurately includes all three excursions, lacking none, and includes no spurious excursions from any outlying echo.

(4) A memory cell can be forced to change its state by any detectable excursion. Here, "detectable" implies a signal strength larger than the hysteresis, or deliberate "dead" or "backlash" zone in the cell's response threshold.

The flip-flop-flip method causes a memory cell to reverse its state to comply with the direction of zero-crossing due to the echo pulse waveform, and then to hold that state until again forced to reverse. It literally flips (and flops) to "down-up-down" for a pulse of waveform 10, shown in FIG. 1, "neither knowing nor caring" that the amplitude of the central positive excursion 12 is larger than either of the neighboring negative excursions 11 and 13. Because the memory cell is left "down" for a sufficient period of time (unless and until perturbed), it is determined by a matter of simple negation that the waveform of the echo pulse was "up-side-up".

The flaws of the flip-flop-flip method include:

(1) There has to be a carefully regulated "zero," drift-free, against which the zero-crossing can be determined. This zero-crossing level must track the level of the general echo field, and yet not be "pumped" to erroneous levels by strong signals; i.e., it must have agile d.c. restoration capabilities.

(2) The flip-flop-flip technique is easily fooled by complex signals, since it slavishly depends upon the alternation of three excursions.

(3) Like many other methods, it fails when placement of the gate window is not exact enough. But the success of this method is quite good when used under conditions where a complete three-part echo can be obtained, and where that echo is singular in nature and comes from a known depth in the target material.

Another and better method can be called the method of "compared dual integrated" signals. It is considerably more versatile. The method is best implemented with two rectifiers, two integrating circuits, buffer amplifiers, and a comparator. It may employ gating that ensures that no signal is given to either integrator except during a preselected gating interval, or, conversely, clamps both integrators to near electrical ground in spite of the presence of signal except during desired gating intervals. The purpose of the integration is to enable comparison of the amplitudes of peaks of opposite polarity, even though they are not coincident in time. The integrators store each peak long enough so that their amplitudes can be compared. If a negative-going signal dominates, the comparator swings one direction. Conversely, if a positive-going signal dominates, the comparator swings the other direction. At the end of the gating interval, before the integrators can "leak" back appreciably toward their rest value (or before they are deliberately re-clamped to near ground or another selected "zero" level), the output of the comparator is interrogated for polarity, corresponding to phase of the reflected ultrasonic signals.

One advantage of the compared dual integrated technique is that the amplitudes of the signal excursions are examined, rather than relying upon a presumption of a certain choreography for their changes of polarity, as in the flip-flop-flop method. Moreover, the compared dual integrated method is more forgiving with respect to gate timing. It is not essential that all three excursions be gated; only the large central excursion in each echo pulse is needed. In fact, badly distorted echoes, with spurious inclusions, and even missing or compressed area are well handled, presuming only that the central excursion is energetically dominant and is well represented within the gating interval.

There are some disadvantages. The signal amplitudes must be high enough to swamp the knees of the threshold voltages of the rectifiers (typically medium- to low-barrier Schottky diodes with thresholds of 0.15 to 0.35 volts), or some other method of compensation for that threshold voltage must be utilized. Moreover, there must be good balance in the integration elements, high stability in any clamp circuitry used, and fast, symmetrical response in the comparator. Also, although gating is not so critical as in other techniques, it is essential to include the central portion of the echo, as no method can see what is not there.

With respect to the amplitude (as opposed to the phase) of the signal, it is a boon that the compared dual integrated method also replaces any need for a sample-and-hold circuit prior to digitization of the echo signals for use in an image display such as a cathode ray tube. The same signals as are fed to the comparator can also be applied to an operational amplifier, with their polarities appropriately conditioned, to sum the total peak values (both senses of excursions included) and are automatically held for digitization by the integrators already in use for phase polarity detection.

Implicit in the effective use of phase or polarity information is the convenient and meaningful display of that information. A preferred method of digitization displays signals of negative and positive polarity (phase) at opposite ends of a continuum. The output of the phase (polarity) comparator is used both as a most significant bit in the digital word of each product byte, and also as a control for a ones-complement inversion of the less significant bits. In this way the product byte, regardless of its size, can be made to map a broad range of echo signal polarities and amplitudes. The binary value of the byte will change smoothly from 0000xxx000 to 0111xxx111 when ranging from the largest inverted echo amplitude toward the smallest (no echo), then continues to count up smoothly from 1000xxx000 to 1111xxx111 as it proceeds from the smallest non-inverted echo to the largest non-inverted echo. (Here, "xxx" means any number of intermediate value bits, in a regular binary count sequence.) The advantage of a concomitant but distinct display of complementary echo values is a tremendous improvement in signal interpretation. Once arranged in a monotonic continuum, the numbers are available for numerous types of significant processing, such as (1) direct mapping of acoustic impedances 2) structure-type recognition software (3) color-mapping with false-color images which distinctly and sensibly inform the operator of the nature of the sample material.

From the foregoing description, it will be apparent that the present invention encompasses methods of examining internal structure in an object by reflection mode scanning acoustic microscopy, comprising various combinations of the steps of:

A. Generating a series of acoustic pulses of ultrasonic frequency and predetermined magnitude B. Insonifying an object with the acoustic pulses, with predetermined timing and in accordance with a preselected scanning pattern.

C. Receiving ultrasonic pulse echoes reflected from the object and developing an initial electrical signal comprising a sequence of electrical pulses of varying amplitudes and polarities representative of the magnitudes and phases, respectively, of the ultrasonic pulses echoes.

D. Gating the initial electrical signal on and off for a variety of purposes and effects; gating may be performed in conjuction with and concurrently with the integrations of steps E and F (below) prior to such integrations, and/or subsequent thereto.

E. Integrating the positive-going pulses in the initial electrical signal to develop a positive polarity sub-signal representative of a first phase of the reflected ultrasonic energy.

F. Integrating the negative-going pulses in the initial electrical signal to develop a negative polarity sub-signal representative of a second phase of the reflected ultrasonic energy.

G. Combining the two sub-signals on the basis of absolute amplitude, independent of polarity, to develop an amplitude content signal.

H. Comparing the two sub-signals on the basis of the combination of amplitude and polarity to develop a polarity content signal.

I. Modifying the amplitude content signal in accordance with the polarity content signal to develop an image signal comprising a data continuum having twice the range of the amplitude content signal.

X. Finally, producing a unified image representative of of the object, the unified image simultaneously displaying positions, magnitudes, and directions of acoustic impedance transistors for at least one depth level of the object. In the unified image:
1. positions of the acoustic transitions in the image and the image level in the object are determined by the timing of the pulses in the initial electrical signal,
2. transitions between differing acoustic impedances at the surfaces of and within the object are determined by the amplitudes of the pulses in the initial electrical signal, and
3. increases and decreases in acoustic impedance, in transitions at the surfaces of and within the object, are determined by the polarities of the pulses in the initial electrical signal.

A number of modifications can be made in the above technique, with merit in some situations. Two notable ones are:
(1) Use of the "compared dual integrated" method with no direct gate at all, simply by interrogating the polarity comparator and the amplitude amplifier for phase and amplitude, respectively, at chosen intervals; or,
(2) Rapid interrogation of both of these devices, or of the integrators (many times during the period of a pulse ... or at least as many times as is necessary to fulfill the requirements of information theory ... i.e. at least twice the frequency of the bandwidth of the information desired), and the integration or combination, over some longer period, of the information so obtained. This multiplex interrogation of the amplifier and comparator and the integration or combination of the results obtained can be done in either digital or analog format. In a digital format, the amplitude information is directly digitized at each interrogation; the penalty here is merely the necessity for very fast analog-to-digital conversion circuitry. The phase information is inherently digital, but in some cases may jitter, though in this scheme it can be un-noised by majority logic. In the analog technique, the amplitude information is sampled each time, and summed by some method of charge accumulation; the result is digitized only at the completion of the longer interval.

The refinement of the rapid multiple interrogation method is that equal weightings are given to very small slices of time, which may contain very narrow peaks that otherwise would be less prominent in the signal value. Also, the sequential values obtained can be examined, each in turn, to see if they are larger than a certain threshold, and also if they are the largest yet obtained. In this manner, over the course of a given sequence of echoes, the largest echoes can be assembled into a queue; a parallel digital queue would accompany them, representing the time-of-flight of each detected event. The need for a "gate" per se would be eliminated. As a result, a small coterie of most prominent echoes defines the echo field, and is capable of doing a rough and ready form of tomography, again within the restrictions of the beamwaist/resolution criterion.

Of special interest in the method of the present invention are:
(1) Detection of both phases of reflected ultrasonic pulse signals.
(2) Processing of this information into a format which preserves both the continuum of the information, in an amplitude sense, and the phase (polarity) information for the echoes, so that this information can be freely moved through digital processing methods without further encoding or packaging.
(3) A unified display that incorporates both phases (polarities) of echo, in a manner which preserves the intuitive relationships of phase and amplitude, for instant examination by an investigator, without further encoding or packaging ... except insofar as false-color mapping can be used to further sensiblize the actual display.
(4) Detection and comparison of both polarities essentially simultaneously.
(5) Extensions of the method to other arrangements of value, such as extension of the frequency coverage of the echo evaluation, the potential elimination of a gate, and the analysis, in one rather simple package, of many layers, or depths of received echo, both in raw form (within the constraints of the beamwaist width and apparent spot-size), and in processed form (by rather simple neighboring-sample relationship tomographic reconstruction especially when outside the range of the classical direct spot-size constraints), such extended methods including such modifications as alteration of the rate and multiplicity of interrogation of the detector outputs as discussed above.

As a simple case, consider a three-bit analog-to-digital converter (ADC), which takes an incoming amplitude of from zero to one volt, and converts to digital form. There are only eight possible states, in decreasing order:

| | |
|---|---|
| 111 | maximum voltages (one volt) |
| 110 | high-intermediate voltages |
| 101 | high-intermediate voltages |
| 100 | mid-range voltages |
| 011 | mid-range voltages |
| 010 | low-intermediate voltages |
| 001 | low-intermediate voltages |
| 000 | voltages near zero |

See FIG. 4A. Of course, the order can be reversed. With the absolute magnitudes of echo pulses utilized, there is superposition of the negative and the positive signals. Both types of strong discontinuity read high up on the scale, but they are essentially indistinguishable as between hard and soft discontinuities or transitions.

In the preferred method of the invention, for steps G, H and I above the phase polarity bit is used as an additional and most significant bit, in this example a fourth bit. Whenever it is a "1", the remaining three bits are not inverted, remaining as they were. Whenever it is a "0", the original three bits are inverted. In this way, the coding is expanded in the negative direction and the most negative signals are represented as opposite the most positive; see FIG. 4B, in which the new most significant bit is the initial bit, enclosed in parentheses. When that bit is a zero, the bits following it are merely the complements of those in the original magnitude column.

| Magnitude: | Sign: | Meaning: | Becomes: |
|---|---|---|---|
| 111 | + | most positive | (1)111. |
| 110 | + |  | (1)110. |
| 101 | + |  | (1)101. |
| 100 | + | intermediate | (1)100. |
| 011 | + |  | (1)011. |
| 010 | + |  | (1)010. |
| 001 | + |  | (1)001. |
| 000 | + | zero or just + | (1)000. |
| 000 | − | zero or just − | (0)111. |
| 001 | − |  | (0)110. |
| 010 | − |  | (0)101. |
| 011 | − |  | (0)100. |
| 100 | − | intermed neg | (0)011. |
| 101 | − |  | (0)010. |
| 110 | − |  | (0)001. |
| 111 | − | most negative | (0)000. |

This same scheme can be directly extended to word lengths of any size, instead of the three bits described and portrayed in FIGS. 4A and 4B; the end result is a data continuum in which positive and negative polarities are at opposite extremities; that data continuum is easily usable in creating a readily interpreted visual image.

If a grey scale were placed at the edge of a CRT display, as a key to indicate phase polarity of the echoes, it could appear similar to the illustration in FIG. 5A. The top of the grey scale or brightness continuum is quite dark, for a maximum amplitude echo signal of positive polarity. The bottom is very light, representative of a maximum amplitude negative-polarity pulse echo signal. Of course, this brightness continuum could be reversed. Intermediate values are a range of greys. With digital bytes of reasonable length, as discussed above, there would be many more grey tones. When an image appears on screen, containing both higher- and lower-impedance features, they are seen as quite distinct from each other. Thus, in FIG. 5B, in the image 40 a low-impedance discontinuity or imperfection 41, such as a void, is shown as being very light. A high-impedance transition, shown as a dark spot 42, would be some "hard" inclusion. Image 40 thus incorporates both phases of the echo simultaneously in a manner that permits prompt, ready interpretation by an investigator, with no further encoding or packaging required. The same useful effect can be realized and even improved, by using a color scale for the image instead of the grey scale of FIG. 5A. Furthermore, different levels in the acoustically scanned object can be shown in different color combinations, of varying brighness in each, superimposed in image 40 to give maximized information regarding the object.

FIG. 6 affords a simplified block and schematic illustration of a scanning acoustic microscope 50 that incorporates a display system constructed in accordance with one embodiment of the invention. SAM 50 includes a tank 51, shown in section, filled with a sonic medium 52 which is usually water, though other liquids may be employed. An object 53 to be examined by microscope 50 is supported in medium 52; for simplification, the support has not been shown. The target object 53 includes a plastic member 54 bonded to a metal member 55. In general, the bond 56 between members 54 and 55 is sound. However, member 53 is shown as including a "hard" discontinuity 57 and a "soft" discontinuity 58 between plastic 54 and metal 55. The soft inclusion 58 may be a void.

SAM 50 includes a transducer unit 61 that extends into acoustic medium 52, being located immediately above target object 53. Transducer 61 includes an output transducer for generating a seris of acoustic pulses of ultrasonic frequency and predetermined magnitude in response to an electrical input signal. Transducer unit 61 also includes a receiver for receiving ultrasonic pulse echoes from object 53; the receiver develops an initial electrical signal comprising a sequence of electrical pulses of varying amplitudes and polarities representative of the magnitudes and phases, respectively, of those ultrasonic echoes. The construction of transducer unit 61 may be quite conventional and hence is not shown in detail. Usually, the output transducer and the receiver in unit 61 may share one physical mechanism, which functions part of the time in a manner analogous to an electromagnetic speaker and the remainder of the time in a manner analogous to an electromagnetic microphone.

SAM 50, FIG. 6, further comprises an ultrasonic electrical signal generator 63 connected to a gate 64. Gate 64 has a second input derived from a timing signal generator 65. Gate 64 may include additional circuits, such as matching networks and pulse defining and shaping circuits, of the sort necessary to generate appropriate pulses so that the electrical signal supplied from gate 64 to transducer unit 61 has the desired waveform, frequency, and timing characteristics. As previously noted, the preferred waveform for the acoustic pulse output from transducer unit 61 is as shown in FIG. 1.

Scanning acoustic microscope 50 also includes an appropriate scanning mechanism for moving transducer unit 61 transversely, as indicated by arrows A and B, relative to target object 53. Such a scanning mechanism enables transducer unit 61 to direct its output of ultrasonic pulses toward object 53 to insonify that object in accordance with a preselected scanning pattern. Appropriate scanning mechanisms most suitable for this purpose are described and claimed in the co-pending patent application of Frank J. Cichanski Ser. No. 44,419, filed Apr. 30, 1987.

In SAM 50, FIG. 6, gate 64 is connected to the output transducer in unit 61. The receiver in unit 61 has its output connected to an initial upstream receiver gate 67. Gate 67 also has a second signal input from timing signal generator 65 that may have the same frequency as the gate signal applied to circuit 64 but is usually displaced in time so that the two gates are not open simultaneously. That is, the output from transducer 61 is gated on and off in gate 67 at the same frequency as used in pulse gate 64. Other timing arrangements for gate 67 may also be utilized. The output from gate 67 is supplied to an amplifier 68.

The circuitry and mechanism of SAM 50, as thus far described, are essentially conventional. Transducer unit 61 utilizes the input signal from gate 64 to generate a series of acoustic pulses of ultrasonic frequency and predetermined magnitude, preferably a sequence of pulses having the configuration illustrated in FIG. 1. This beam is directed toward and insonifies object 53 with predetermined timing and in accordance with a predetermined scanning pattern, developed by movement of transducer 61 across the face of object 53. Ultrasonic echoes reflected from the surfaces and from the interior of object 53 are intercepted and detected, again by transducer unit 61, and utilized to generate an initial electrical signal comprising a sequence of electrical pulses of varying amplitudes and polarities representative of the magnitudes and phases, respectively, of the ultrasound echoes. It is this initial electrical signal that is supplied to the remainder of the display system through gate 67 and amplifier 68.

The output of amplifier 68 is connected to two oppositely polarized Schottky diodes 71 and 72. Diode 71 is in turn connected to an integrator circuit 73, shown simply as a capacitor in parallel with a resistor, returned to system ground. Similarly, diode 72 is connected to an integrator circuit 74 that is returned to system ground. A gate circuit 75 is connected in parallel with integrator 73. The integrator gate 75 has a control input supplied from timing signal generator 65. Another integrator gate 76 is connected in parallel with integrator 74. It also has an input from timing signal generator 65, which may be the same control signal that is supplied to gate 75.

An output line 77 from diode 71 and integrator 73 is connected to an amplifier circuit 80 that includes an operational amplifier 81. The input connection includes two resistors 82 and 83 connected in series from conductor 77 to system ground, with the junction of the two resistors connected to the plus input of operational amplifier 81. Similarly, the output conductor from diode 72 and integrator 74 is connected to a resistor 84 that is in turn connected to the minus input of operational amplifier 81. An additional resistor 85 is connected between resistor 84 and the output of device 81. The output of amplifier 80 is connected to a digitizing circuit 86. Digitizer 86 has an additional input from timing signal generator 65.

SAM 50, FIG. 6, further comprises a phase or polarity comparator 87. Comparator 87 has two inputs, one from each of the conductors 77 and 78. The output of comparator 87 affords a second input to digitizing circuit 86. The output from digitizing circuit 86 is connected to display signal circuits 88 that are a part of a cathode ray tube display 90. A memory 89 is preferably interposed between digitizer 86 and display circuits 88.

In considering operation of the display system of SAM 50, a convenient starting point is the two complementary detectors 71 and 72, here shown as simple Schottky barrier diodes. For best sensitivity, these diodes can be current-biased to places on their rectifying "knees" that maximize their sensitivity and ability to discriminate very low signals of the appropriate polarity. Of course, other high speed rectifiers can be utilized. On each excursion of the initial electrical signal that is supplied to the diodes from amplifier 68, one of the two rectifiers 71 and 72 is driven to conduction. In this manner, the initial electrical signal is detected and directed to one or the other of the two integrators 73 and 74, depending upon instantaneous polarity.

In FIG. 6, integrators 73 and 74 are each shown as a simple capacitor in parallel with a resistor. More complex integrator circuits may be utilized if desired. On the other hand, even the parallel resistors may be unnecessary in some circuits, where their function may be effectively supplied by the leakage resistances of rectifiers 71 and 72 and the integrator capacitors.

The capacitors of integrators 73 and 74, as a result of the alternating rectification, are charged in accordance with excursions of the input signal of alternating polarity. Actually, the charge on each integrator capacitor is proportional to the current each receives from the initial electrical signal, which in turn is proportional to the net voltage appearing across the rectifiers divided by their intrinsic impedance. By carefully matching integrators 73 and 74, and appropriate selection of capacitor size, the voltage appearing upon each integrator capacitor can be made to be a very good index of one polarity of excursion of the initial electrical signal. The resistors in the integrators, whether actual or virtual, may serve to reset the integrators to system ground; a relatively short reset interval is utilized.

Instead of or in addition to the resistors in integrators 73 and 74, gates 75 and 76 may be utilized to control the intervals of charge and discharge for the capacitors of integrators 73 and 74. Gates 75 and 76 are each kept conductive for a substantial portion of each cycle of the beam gate frequency referred to above, based on appropriate input signals from timing signal generator 65. These gates or switches are each opened briefly in each cycle of the beam gate frequency, when it is desired to charge their integrator capacitors. In this arrangement, though the initial electrical signal from amplifier 68 is supplied continuously to rectifiers 71 and 72 and integrators 73 and 74, the integrator capacitors are not charged except for those brief intervals when the gates are open. Typically, gates 75 and 76 may be gallium arsenide devices or other high speed switches.

The output signal on conductor 77 is a positive polarity sub-signal having an amplitude representative of excursions of the reflected ultrasonic energy in one direction or phase. The signal on conductor 78, on the other hand, is a negative polarity sub-signal representative of a second phase of the ultrasonic echoes. Thus, the two separate signals on conductors 77 and 78 represent the amplitudes and polarities of all excursions of the initial electrical signal, and hence of the ultrasonic echo signals, over intervals which can be made as long or as short as necessary within reasonable limits. These two signals, accordingly, can be compared to determine the net phase or polarity of the echo pulses.

This comparison is done in circuit 87. Again, gallium arsenide or other high speed components can be used in comparator 87; on the other hand, the comparison can be realized on a less expensive basis, yet suitable for most purposes, through utilization of silicon integrated circuits or other such devices. Comparator 87 simply gives a digital output of one value, usually a "high" output, if the amplitude at its positive polarity sub-signal input from line 77 exceeds the amplitude of the negative polarity sub-signal input from line 78. Conversely, comparator 87 affords a digital "low" output when the reverse amplitude relationship occurs. Thus, the output of comparator 87 is a polarity content signal, representative of the dominant polarity of a brief segment of the initial electrical signal. It no longer conveys, and hence is essentially independent of, amplitude information.

The output from comparator 87 serves two purposes. It becomes the most significant digit of the final binary byte in the output signal from digitizing circuit 86, corresponding to the digit in parentheses in FIG. 4B. The output from comparator 87 also serves to regulate interpretation of all of the less-significant bits for each byte in the output signal from digitizing circuit 86, entailing inversion of negative-going bits as discussed above. This is the signal processing that enables circuit 86 to generate a data continuum mapping all of the available information from the scanned object, object 53, as described above.

Amplifier 80, on the other hand, utilizes the two input signals from lines 77 and 78 to generate an amplitude content signal representative of the amplitude of the initial electrical signal, independent of polarity. To meet the most intensive high speed requirements, operational amplifier 81 may comprise a gallium arsenide or other high speed operational amplifier. On the other hand, in many SAM systems, readily available and less expensive operational amplifiers may be used. In amplifier 80 the combined amplitudes of the positive and negative signal excursions on conductors 77 and 78 are summed and supplied to digitizing circuit 86 for analog-to-digital conversion. When the output from digitizing circuit 86 is at a maximum, due to a high input from amplifier 80, and the input from comparator 87 signifies a positive polarity, then the binary signal supplied to display circuits 88 is of the form (1)111xxx111. On the other hand, if the output of comparator 87 indicates a negative signal, then the output from digitizing circuit 86 is inverted to the form (0)000xxx000. All intermediate values fall into place, as previously discussed in connection with FIG. 4B, affording a smooth continuum mapped upon binary words of bit length one longer than the bit length of the ADC circuitry used in unit 86. As previously noted, the binary data continuum can be reversed if desired.

FIG. 6 shows gate 67 in the input circuit from transducer unit 61 to the image display circuitry and gates 75 and 76 in parallel with integrators 73 and 74. Gating can also be accomplished in the outputs of circuits 80 and 87 or even farther downstream in the display system. Gate 67 usually performs a general gating function to eliminate major sources of extraneous noise, with gates 75 and 76 and any other additional gates, wherever located, establishing more critical windows for the image 53A displayed by monitor 90, in which discontinuity images 57A and 58A are shown, representing the discontinuities 57 and 58 in object 53. It is not always essential to have multiple gating arrangements. In some instances, gate 67 or gates 75 and 76 may be adequate.

Memory 87 may be used to facilitate development of a multi-level image of the object under acoustical examination. Thus, in any SAM acoustic reflections may occur from several levels of an object; see the discussion of FIGS. 2A and 2B. Appropiate gating or other timing differentiation makes it possible to separate the pusles echoed from different levels in the object. If pulses reflected from two or more levels are segregated and recorded in the memory, a composite, multi-level image can be developed on monitor 90. The object levels are conveniently differentiated, in the display, by using different colors for separate levels.

In digitizing circuit 86, as previously noted, the amplitude content and polarity content signals from preceding circuits 80 and 87 are preferably combined to develop a data continuum signal in the manner described above in connection with FIG. 4B. This data continuum can be mapped, in image 53A, in several ways. The simplest technique, and the preferred arrangement if unit 90 is a monochrome display, is to reproduce the data continuum as a brightness continuum. With a color display, there is greater versatility; the data continuum can be reproduced in image 53A as a color spectrum, a combination of a brightness continuum and a color spectrum, or a brightness spectrum combined with arbitrary color differentiation (e.g., for different levels in the object).

I claim:

1. The method of examining internal structure in an object by reflection mode scanning acoustic microscopy, comprising the steps of:
    (A) generating a series of acoustic pulses of ultrasonic frequency and predetermined magnitude;
    (B) insonifying an object with the acoustic pulses from step A, with predetermined timing and in accordance with a preselected scanning pattern;
    (C) receiving ultrasonic pulse echoes reflected from the object and developing an initial electrical signal comprising a sequence of electrical pulses of varying amplitudes and polarities representative of the magnitudes and phases, respectively, of the ultrasonic pulse echoes; and
    (X) producing a unified image representative of structure of the object, the unified image simultaneously displaying positions, magnitudes, and directions of acoustic impedance transitions for at least one depth level of the object, in which image:
        (1) positions of the acoustic transitions in the image and the image level in the object are determined by the timing of the pulses in the initial electrical signal,
        (2) transitions between differing acoustic impedances at the surfaces of and within the object are determined by the amplitudes of the pulses in the initial electrical signal, and
        (3) increases and decreases in acoustic impedance, in transitions at the surfaces of and within the object, are determined by the polarities of the pulses in the initial electrical signal.

2. A method of scanning acoustic microscopy, according to claim 1, comprising the following additional step:
    (D) gating the initial electrical signal on and off at a predetermined frequency to limit that signal to desired information; and
    utilizing the gated initial electrical signal to produce the image of step X.

3. A method of scanning acoustic microscopy, according to claim 1, comprising the following additional steps:
    (E) integrating the positive-going pulses in the initial electrical signal to develop a positive polarity sub-signal representative of a first phase of the reflected ultrasonic energy;
    (F) integrating the negative-going pulses in the initial electrical signal to develop a negative polarity sub-signal representative of a second phase of the reflected ultrasonic energy; and
    utilizing the sub-signals to produce the image of step X.

4. A method of scanning acoustic microscopy, according to claim 3, comprising the following additional step:
    (D) gating the initial electrical signal on and off at a predetermined frequency to limit that signal to desired information; and
    utilizing the gated initial electrical signal in steps E and F.

5. A method of scanning acoustic microscopy, according to claim 4, in which the gating of step D is performed in conjunction with and concurrently with the integrations of steps E and F.

6. A method of scanning acoustic microscopy, according to claim 3, comprising the following additional steps:

(G) combining the two sub-signals on the basis of absolute amplitude, independent of polarity, to develop an amplitude content signal; and (H) comparing the two sub-signals on the basis of the combination of amplitude and polarity to develop a polarity content signal; and utilizing the amplitude and polarity content signals in carrying out step X.

7. A method of scanning acoustic microscopy, according to claim 6, comprising the following additional step:

(I) modifying the amplitude content signal in accordance with the polarity content signal to develop an image signal comprising a data continuum having twice the range of the amplitude content signal; and utilizing the image signal to produce the image in step X.

8. A method of scanning acoustic microscopy, according to claim 7, comprising the following additional step:

(D) gating the initial electrical signal on and off at a predetermined frequency to limit that signal to desired information; and utilizing the gated initial electrical signal in steps E and F.

9. A method of scanning acoustic microscopy, according to claim 8, in which the gating of step D is performed in conjunction with and concurrently with the integrations of steps E and F.

10. A method of scanning acoustic microscopy, according to claim 9, in which the gating of step D is also carried out prior to the integrations of steps E and F.

11. A display system for a scanning acoustic microscope of the kind comprising transducer means for generating a series of acoustic pulses of ultrasonic frequency and predetermined magnitude, acoustic scanning means for directing the acoustic pulses to impinge upon and insonify an object with predetermined timing and in accordance with a preselected scanning pattern, and receiver means for receiving ultrasonic pulse echoes reflected from the object and developing an initial electrical signal of varying amplitude and polarity representative of the magnitude and phase, respectively, of the ultrasonic pulse echoes, the display system comprising:

amplifier means, connected to the receiver means, for generating an amplitude content signal representative of amplitude of the initial electrical signal, independent of polarity;

comparator means, connected to the receiver means, for generating a polarity content signal representative of polarity of the initial electrical signal, independent of amplitude; and display means, actuated by the content signals, for displaying a unified image of the object in which acoustic impedance transitions for at least one depth level of the object from which echoes of different polarities occur are clearly distinguished from each other in the image despite similarities, however close, in the magnitudes of those echoes.

12. A display system for a scanning acoustic microscope according to claim 11 and further comprising integrator means connected to the receiver means, ahead of the comparator means, the integrator means including:

a first integrator for integrating the positive-going components of the initial electrical signal to develop a positive polarity sub-signal representative of a first phase of the ultrasonic echoes; and a second integrator for integrating negative-going components for the initial electrical signal to develop a negative polarity sub-signal representative of a second phase of the ultrasonic echoes.

13. A display system for a scanning acoustic microscope according to claim 12 in which the integrator means is also interposed between the receiver means and the amplifier means.

14. A display system for a scanning acoustic microscope according to claim 13 and further comprising:

integrator gate means, connected to both integrators, for gating the integrators on and off at a predetermined frequency.

15. A display system for a scanning acoustic microscope according to claim 13 and further comprising:

means for modifying the amplitude content signal in accordance with the polarity content signal to develop an image signal comprising a data continuum having twice the range of the amplitude content signal;

the display means being actuated by the image signal.

16. A display system for a scanning acoustic microscope according to claim 15 and further comprising:

integrator gate means, connected to both integrators, for gating the integrators on and off at a predetermined frequency.

17. A display system for a scanning acoustic microscope according to claim 16 and further comprising initial signal gate means for gating the initial electrical signal on and off at a predetermined frequency.

18. A display system for a scanning acoustic microscope according to claim 11 and further comprising:

initial signal gate means for gating the initial electrical signal on and off at a predetermined frequency.

19. A display system for a scanning acoustic microscope according to claim 18 and further comprising integrator means connected to the receiver means, ahead of the comparator means, the integrator means including a first integrator for integrating positive-going components of the initial electrical signal to develop a positive polarity sub-signal representative of a first phase of the ultrasonic echoes; and a second integrator for integrating negative-going components of the initial electrical signal to develop a negative polarity sub-signal representative of a second phase of the ultrasonic echoes.

20. A display system for a scanning acoustic microscope according to claim 19 in which the integrator means is also interposed between the receiver means and the amplifier means.

21. A display system for a scanning acoustic microscope according to claim 20 and further comprising:

means for modifying the amplitude content signal in accordance with the polarity content signal to develop an image signal comprising a data continuum having twice the range of the amplitude content signal;

the display means being actuated by the image signal.

22. A display system for a scanning acoustic microscope according to claim 21 in which the display means comprises means for reproducing the data continuum, in the image, as a brightness continuum.

23. A display system for a scanning acoustic microscope according to claim 21 in which the display means comprises means for reproducing the data continuum, in the image, as a continuous color spectrum.

24. A display system for a scanning acoustic microscope according to claim 22 in which the display means comprises means for reproducing different portions of the data continuum, in the image, in different colors.

25. A display system for a scanning acoustic microscope according to claim 11 and further comprising:
   means for modifying the amplitude content signal in accordance with the polarity content signal to develop an image signal comprising a data continuum having twice the range of the amplitude content signal;
   the display means being actuated by the image signal.

26. A display system for a scanning acoustic microscope according to claim 25 in which the display means comprises means for reproducing the data continuum, in the image, as a brightness continuum.

27. A display system for a scanning acoustic microscope according to claim 25 in which the display means comprises means for reproducing the data continuum, in the image, as a continuous color spectrum.

28. A display system for a scanning acoustic microscope according to claim 25 in which the display means comprises means for reproducing different portions of the data continuum, in the image, in different colors.

* * * * *

Notice of Adverse Decisions in Interference

In Interference No. 102,428, involving Patent No. 4,866,986, F. J. Cichanski, METHOD AND SYSTEM FOR DUAL PHASE SCANNING ACOUSTIC MICROSCOPY, final judgment adverse to the patentee was rendered Jan. 23, 1992, as to claims 1-6 and 11.

*(Official Gazette August 25, 1992.)*